United States Patent [19]

Effland et al.

[11] Patent Number: 5,202,319
[45] Date of Patent: Apr. 13, 1993

[54] SUBSTITUTED 3-AMINO-2,3,4,5-TETRAHYDRO-1-ARYLOXY-3-BENZAZEPINES

[75] Inventors: Richard C. Effland; Joseph T. Klein, both of Bridgewater, N.J.

[73] Assignee: Hoechst-Roussel Pharmaceuticals Inc., Somerville, N.J.

[21] Appl. No.: 763,711

[22] Filed: Sep. 23, 1991

[51] Int. Cl.$^5$ ............... A61K 31/55; C07D 223/16
[52] U.S. Cl. ................................ 514/213; 540/594
[58] Field of Search ..................... 514/213; 540/594

[56] References Cited

U.S. PATENT DOCUMENTS 4,314,081  2/1982  Molloy et al. ............... 564/103
4,794,181 12/1988  Effland et al. ............... 540/594

OTHER PUBLICATIONS

Asberg, et al., Science, vol. 198, 1976, pp. 478–480.
Horn, et al., Br. J. Pharmac. (1974) 51, 399–403.
Shasken et al., J. Pharmacol. and Exp. Therapeutics 1970, vol. 173 (2) pp. 404–418.
Mitsuhashi, et al., Chemical Abstracts, vol. 71, 1969, Abstract 338.
Shiotani, et al., Chem. Pharm. Bull. 15 (6) 761–767 (1967).
Zbiral et al., Liebigs Ann. Chem. 758 72–83 (1972).
Langer, et al., Science, 210, 1980 pp. 1133–1135.
Lange's Current Medical Diagnosis and Treatment (San Mateo, Calif. Appleton and Lange 1992) pp. 805–807.
Merck Index (Merck and Co., Rahway, N.J., 1990) p. 4116.

Primary Examiner—Mukund J. Shah
Assistant Examiner—E. C. Ward
Attorney, Agent, or Firm—Tatsuya Ikeda

[57] ABSTRACT

There are disclosed various compounds of the formula below,

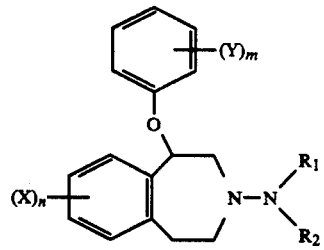

where
n is 1 or 2;
m is 1 or 2;
each X is independently hydrogen or loweralkoxy;
Y is hydrogen, halogen or trifluoromethyl;
$R_1$ is hydrogen, loweralkyl, arylloweralkyl, heteroarylloweralkyl, pyridinyl, loweralkylcarbonyl, arylloweralkylcarbonyl, heteroarylloweralkylcarbonyl, trifluoromethylcarbonyl or arylcarbonyl; and
$R_2$ is hydrogen, loweralkyl, loweralkoxycarbonyl, aminoloweralkylcarbonyl, loweralkylaminoloweralkylcarbonyl or diloweralkylaminoloweralkylcarbonyl;

which are useful as modulators of neurotransmitter function such as serotonergic and adrenergic, and as such are useful as antidepressants and for the treatment of personality disorders such as obsessive compulsive disorders.

17 Claims, No Drawings

SUBSTITUTED 3-AMINO-2,3,4,5-TETRAHYDRO-1-ARYLOXY-3-BENZAZEPINES

The present invention relates to compounds of the formula,

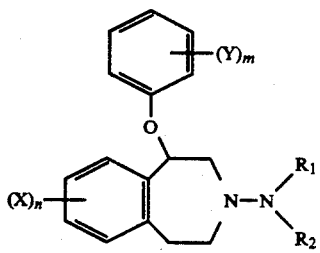

where
n is 1 or 2;
m is 1 or 2;
each X is independently hydrogen or loweralkoxy;
Y is hydrogen, halogen or trifluoromethyl;
R₁ is hydrogen, loweralkyl, arylloweralkyl, heteroarylloweralkyl, pyridinyl, loweralkylcarbonyl, arylloweralkylcarbonyl, heteroarylloweralkylcarbonyl, trifluoromethylcarbonyl or arylcarbonyl; and
R₂ is hydrogen, loweralkyl, loweralkoxycarbonyl, aminoloweralkylcarbonyl, loweralkylaminoloweralkylcarbonyl or diloweralkylaminoloweralkylcarbonyl;
which are useful as modulators of neurotransmitter function such as serotonergic and adrenergic, and as such are useful as antidepressants and for the treatment of personality disorders such as obsessive compulsive disorders.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight-and branched-chain pentyl and hexyl.

The term halogen shall mean fluorine, chlorine, bromine or iodine.

The term aryl shall mean a phenyl group substituted with 0, 1 or 2 substituents each of which being independently loweralkyl, loweralkoxy, halogen or trifluoromethyl.

The term heteroaryl shall mean imidazolyl, thienyl, pyridinyl or pyrrolyl.

Throughout the specification and the appended claims, a given chemical formula or name shall encompass all stereo, optical and tautomeric isomers where such isomers exist.

The compounds of this invention are prepared by utilizing one or more of the synthetic steps described below.

Throughout the description of the synthetic steps, the notations n, m, X, Y, R₁ and R₂ shall have the respective meanings given above unless otherwise stated or indicated.

STEP A

A compound of Formula II where R₃ is

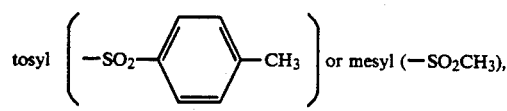

is reduced in a routine manner known to the art (for instance, with the aid of sodium borohydride) to afford a compound of Formula III.

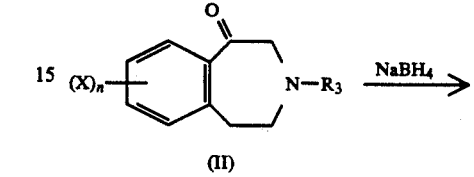

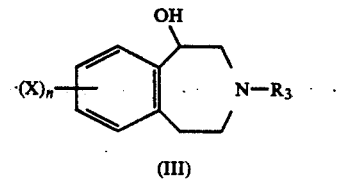

STEP B

Compound III is detosylated or demesylated in a routine manner known to the art (for instance, with the aid of sodium metal in liquid ammonia or sodium bis(2-methoxyethoxy)aluminum hydride in toluene) to afford a compound of Formula IV.

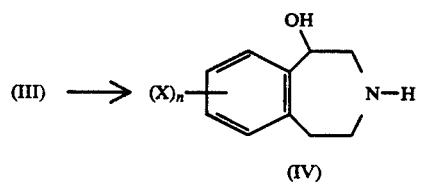

For details of STEPS A and B, the reader is referred to Effland et al., U.S. Pat. No. 4,794,181.

STEP C

Compound IV is allowed to react with a fluoro, chloro or bromo compound of the formula

where Hal is fluorine, chlorine or bromine in a routine manner known to the art, for instance with the aid of NaH in a suitable medium such as dimethylformamide or benzene, to afford a compound of Formula V (Williamson ether synthesis).

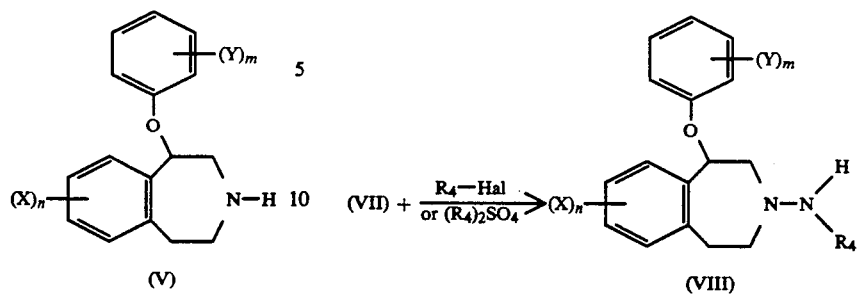

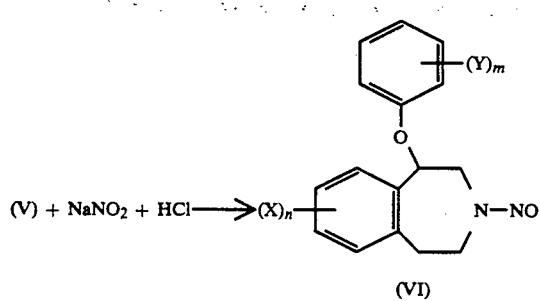

STEP D

Compound V is subjected to a nitrosation reaction conducted in a routine manner known to the art, for instance with the aid of sodium nitrite and hydrochloric acid, to afford a compound of Formula VI.

STEP G

Compound VII is allowed to react with a loweralkyl chloroformate of the formula Cl—CO—OR$_5$ where R$_5$ is loweralkyl to afford a compound of Formula IX. This reaction is typically conducted in a suitable solvent such as dichloromethane in the presence of a suitable base such as sodium bicarbonate or triethylamine at a temperature of about 20°–60° C.

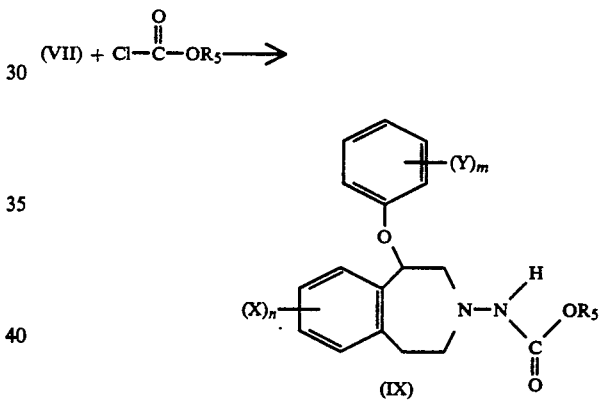

STEP E

Compound VI is reduced with the aid of zinc dust and a suitable acid such as acetic acid in a routine manner known to the art to afford a compound of Formula VII.

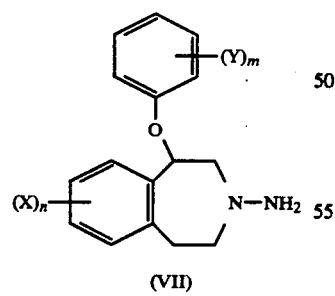

STEP F

Compound VII is allowed to react with a loweralkyl halide of the formula R$_4$—Hal where R$_4$ is loweralkyl and Hal is chlorine or bromine, or with a diloweralkyl sulfate of the formula (R$_4$)$_2$SO$_4$ in a routine manner known to the art to afford a compound of Formula VIII.

STEP H

As a special case where a compound of formula VIII in which the group R$_4$ is methyl is desired, the following method may be employed as an alternative to STEP F. Thus, a compound of formula IXa obtained from STEP G is allowed to react with LiAlH$_4$ in a suitable medium such as tetrahydrofuran at a temperature of about 25°–100° C. to afford a compound of formula VIIIa.

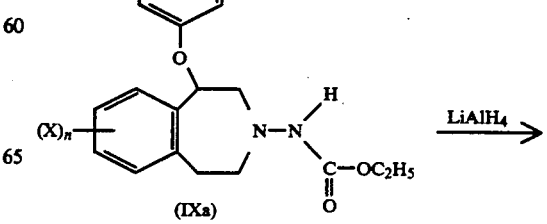

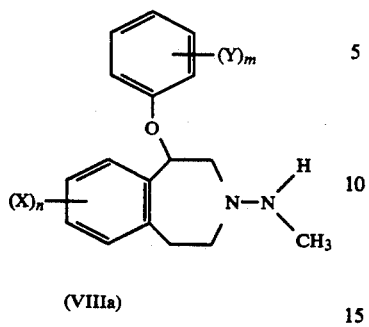

(VIIIa)

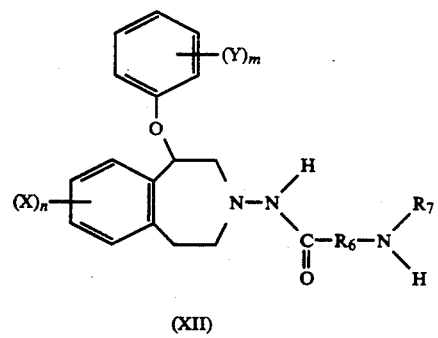

(XII)

STEP I

Compound VII is allowed to react with an acid compound of formula X (in which the amino group is protected) where the group $-R_6-$ represents a loweralkylene group and $R_7$ is hydrogen or loweralkyl in the presence of dicyclohexylcarbodiimide to afford a corresponding ester of formula XI and thereafter the latter is hydrolyzed in a routine manner known to the art or catalytically reduced with hydrogen to afford a compound of formula XII. In this reaction scheme, the same purpose can be accomplished where the benzyloxy moiety in formula X is tertiarybutyloxy.

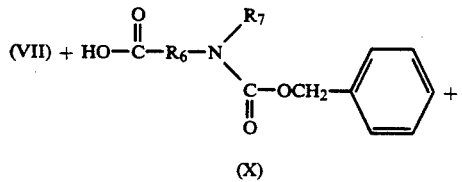

(X)

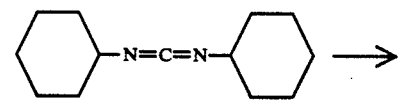

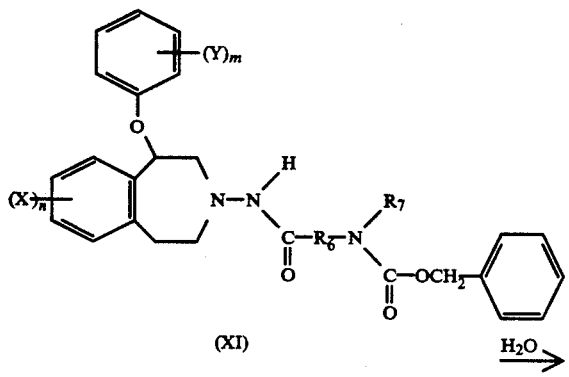

(XI)

STEP J

Compount VII is allowed to react with in acid compound of formula XIII where $R_8$ is loweralkyl and $R_9$ is also loweralkyl in the presence of dicyclohexylcarbodiimide in a routine manner known to the art to afford a compound of formula XIV.

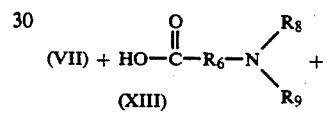

(XIII)

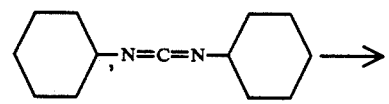

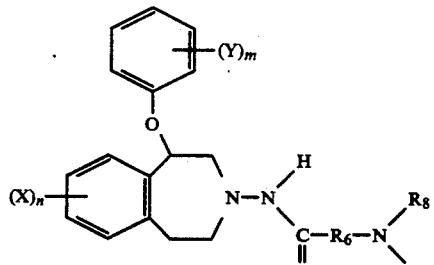

(XIV)

STEP K

A compound of Formula XV obtained from one of the foregoing STEPS is allowed to react with a halide compound of the formula $R_{10}-Hal$ where $R_{10}$ is loweralkyl, arylloweralkyl or heteroarylloweralkyl, or with a diloweralkyl sulfate compound of the formula $(R_{10})_2SO_4$ in substantially the same manner as in STEP F to afford a compound of Formula XVI.

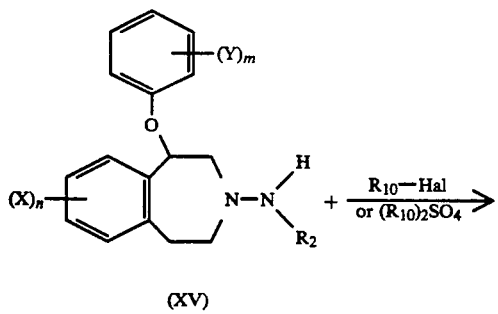

(XV)

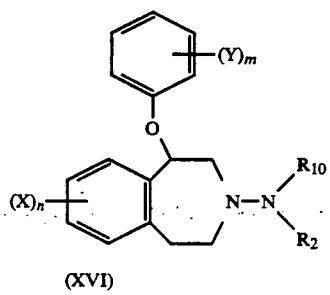

(XVI)

STEP L

Compound XV is allowed to react with an acid halide of the formula $R_{11}$—CO—Hal where $R_{11}$ is loweralkyl, arylloweralkyl, heteroarylloweralkyl, trifluoromethyl or aryl in a routine manner known to the art to afford a compound of formula XVII.

$$(XV) + R_{11}-\overset{O}{\underset{\|}{C}}-Hal \longrightarrow$$

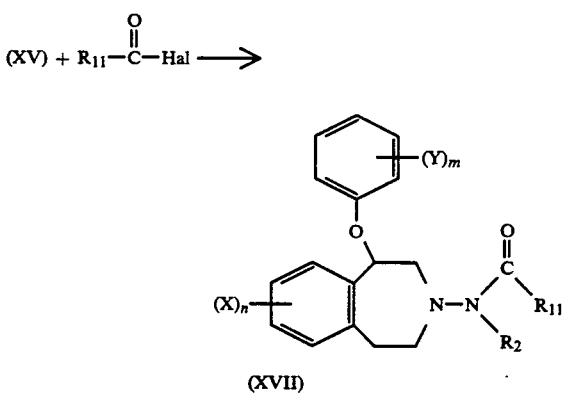

(XVII)

STEP M

As a special case where a compound of formula XVII in which the group $R_{11}$ is trifluoromethyl is desired, the following method may be employed as an alternative to STEP L. Thus, compound XV is allowed to react with methyl trifluoroacetate in the presence of a suitable base such as triethylamine to afford a compound of formula XVIIa. This reaction is typically conducted in a suitable solvent such as anhydrous methanol at a temperature of about 25°–70° C.

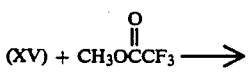

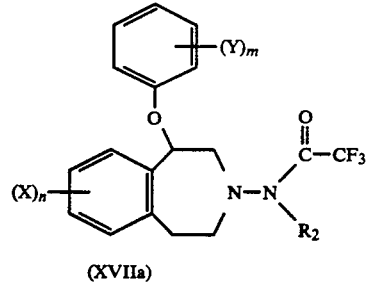

(XVIIa)

STEP N

Compound XV is allowed to react with a fluoro or chloropyridine of formula XVIII where Hal' is fluorine or chlorine to afford a compound of formula XIX. This reaction is typically conducted in a suitable ethereal solvent such as bis(2-methoxyethyl)ether or dioxane, or a polar aprotic solvent such as dimethylformamide.

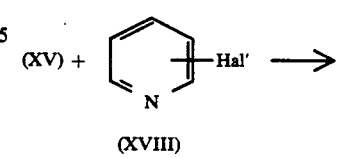

(XVIII)

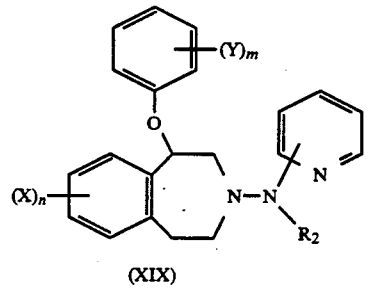

(XIX)

The compounds of Formula I of the present invention are useful as modulators of neurotransmitter function such as serotonergic and adrenergic, and as such are useful as antidepressants and for the treatment of personality disorders such as obsessive compulsive disorders. This utility is manifested in the $^3$H-Serotonin Uptake in Rat Whole Brain Test described below.

$^3$H-Serotonin Uptake in Rat Whole Brain and Hypothalamic Synaptosomes

Purpose

This assay is used as a biochemical screen for potential antidepressants which block serotonin (5HT) uptake.

Introduction

Asberg and coworkers have suggested that subjects with serotonergic hypofunction comprise a biochemical subgroup of depressed patients (1), while others (2) claim that altered serotonergic function determines the mood changes associated with affective disorders. Although the role of 5HT in the etiology of depression is not clear; it is true that a number of antidepressant drugs block the 5HT reuptake mechanism. In vitro receptor binding assays have shown that [$^3$H]-imipramine labels 5HT uptake sites (10) Trazodone and zimelidine are clinically effective antidepressants (3) with fairly selective effects on 5HT uptake (4,5). More recently, fluoxetine has been shown to be both a selective and potent 5HT uptake inhibitor.

[$^3$H]-5HT transport has been characterized in CNS tissue (6,7) and found to be saturable, sodium-and temperature-dependent, inhibited by ouabain, metabolic inhibitors, tryptamine analogs (8) and tricyclic antidepressants (tertiary amines >>secondary amines) (9). The latter findings differentiate 5HT uptake from catecholamine uptake. [$^3$H]-5HT uptake can also be used as a marker for serotonim nerve terminals.

Procedure

A. Animals: Male CR Wistar rats (100-125 g).

B. Reagents

1. Krebs-Henseleit Bacarbonate Buffer, pH 7.4 (KHBB):
Make a 1 liter batch, containing the following salts.

|  | g/L | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add: |  |  |
| Dextrose | 2 mg/ml | 11.1 |
| Iproniazid phosphate | 0.30 mg/ml | 0.1 |

Aerate for 60 min. with 95% O$_2$/5% CO$_2$, check pH (7.4 ± 0.1)

2. 0.32M Sucrose: 21.9 g of sucrose, Q.S. to 200 ml.

3. Serotonin creatinine SO$_4$ is obtained from Sigma Chemical Co. A 0.1 mM stock solution is made up in 0.01N HCl. This is used to dilute the specific activity of radiolabeled 5HT.

4. 5-[1,2-$^3$H(N)]-Hydroxytryptamine creatinine sulfate (Serotonin), specific activity 20-30 Ci/mmol is obtained from New England Nuclear.

The final desired concentration of $^3$H-5HT in the assay is 50 nM. The dilution factor is 0.8. Therefore, the KHBB is made up to contain 62.5 nM [$^3$H]-5HT.

| Add to 100 ml of KHBB. | |
|---|---|
| A) 56.1 μl of 0.1 mM 5HT = | 56.1 nM |
| *B) 0.64 nmole of $^3$H-5HT = | 6.4 nM |
|  | 62.5 nM |

*Calculate volume added from specific activity of $^3$H-5HT.

5. For most assays, a 1 mM solution of the test compound is made up in a suitable solvent and serially diluted such that the final concentration in the assay ranges from $2 \times 10^{-8}$ to $2 \times 10^{-5}$M. Seven concentrations are used for each assay. Higher or lower concentrations may be used depending on the potency of the compound.

C. Tissue Preparation

Male Wistar rats are decapitated and the brain rapidly removed. Either whole brain minus cerebella or hypothalamus is weighed and homogenized in 9 volumes of ice-cold 0.32M sucrose using a Potter-Elvejhem homogenizer. Homogenization should be done with 4-5 up and down strokes at medium speeds to minimize synaptosome lysis. The homogenate is centrifuged at 1000 g for 10 min. at 0°-4° C. The supernatant (S$_1$) is decanted and is used for uptake experiments.

D. Assay

| 800 μl | KHBB + [$^3$H]-5HT |
| 20 μl | Vehicle or appropriate drug concentration |
| 200 μl | Tissue suspension |

Tubes are incubated at 37° C. under a 95% O$_2$/5% CO$_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the means of three determinations. IC$_{50}$ values are derived from log-probit analysis.

References

1. Asberg, M., Thoren, P., Traskman, L., Bertilsson, L., and Ringberger, V. "Serotonin depression:—A biochemical subgroup within the affective disorders. Science 191: 478-480 (1975).
2. DeMontigy, C. Enhancement of 5HT neurotransmission by antidepressant treatments. J. Physiol. (Paris) 77: 455-461 (1980).
3. Feighner, J. P. Clinical efficacy of the newer antidepressants. J. Clin. Psychopharmacol. 1: 235-265 (1981).
4. Ogren, S. O., Ross, S. B., Hall, H., Holm, A. C. and Renyi, A. L. The pharmacology of zimelidine: A 5HT selective reuptake inhibitor. Acta Psychiat. Scand. 290: 127-151 (1981).
5. Clements-Jewry, S., Robson, P. A. and Chidley, L. J. Biochemical investigations into the mode of action of trazodone. Neuropharmacol. 19: 1165-1173 (1980).
6. Ross, S. B. Neuronal transport of 5-hydroxytryptamine. Pharmacol. 21: 123-131 (1980).
7. Shaskan, E. G. and Snyder, S. H. Kinetics of serotonin accumulation into slices from rat brain: Relationship to catecholamine uptake. J. Pharmacol. Exp. Ther. 175: 404-418 (1970).
8. Horn, S. A. Structure activity relations for the inhibition of 5HT uptake into rat hypothalamic homogenates by serotonin and tryptamine analogues. J. Neurochem. 21: 883-888 (1973).
9. Horn, A. S. and Trace, R.C.A.M. Structure-activity relations for the inhibition of 5-hydroxytryptamine uptake by tricyclic antidepressant into synaptosomes from serotonergic neurones in rat brain homogenates. Brit. J. Pharmacol. 51: 399-403 (1974).
10. Langer, S. Z., Moret, C., Raisman, R., Dubocovich, M. L. and Briley M. High affinity [$^3$H]imipramine binding in rat hypothalamus: Association with uptake of serotonin but not norepinephrine. Science 210: 1133-1135 (1980).

Results of the above test are presented in Table 1 for representative compounds of this invention.

TABLE 1

| Compound | Inhibition of $^3$H-serotonin Uptake IC$_{50}$ (μM) |
| --- | --- |
| 3-amino-7,8-dimethoxy-1-phenoxy-2,3,4,5-tetrahydro-3-benzazepine maleate | 2.13 |
| 3-amino-2,3,4,5-tetrahydro-1-(4-trifluoromethylphenoxy)-3-benzazepine maleate (Reference Compound) | 9.36 |
| Fluoxetine | 0.25 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
3-amino-2,3,4,5-tetrahydro-1-(4-trifluoromethylphenoxy)-3-benzazepine;
3-amine-7,8-dimethoxy-1-phenoxy-2,3,4,5-tetrahydro-3-benzazepine;
3,5-dichloro-N-(7,8-dimethoxy-1-phenoxy-2,3,4,5-tetrahydro-1H-3-benzazepin-3-yl)benzamide;
N-[2,3,4,5-Tetrahydro-1-(4-trifluoromethylphenoxy)-3-benzazepin-3-yl]carbamic acid ethyl ester;
N-Methyl-N-[2,3,4,5-tetrahydro-1(4-trifluoromethylphenoxy)-3-benzazepin-3-yl]-carbamic acid ethyl ester;
3-Propylamino-2,3,4,5-tetrahydro-1-(4-trifluoromethylphenoxy)-3-benzazepine;
N-[2,3,4,5-Tetrahydro-1-(4-trifluoromethylphenoxy)-3-benzazepin-3yl]acetamide;
3-Phenylethylamino-2,3,4,5-tetrahydro-1-(4-trifluoromethylphenoxy)-3-benzazepine;
3-Amino-7,8-dimethoxy-2,3,4,5-tetrahydro-1-(4-trifluoromethylphenoxy)-3-benzazepine;
7,8-Dimethoxy-3-methylamino-1-phenoxy-2,3,4,5-tetrahydro-3-benzazepine;
3-Amino-1-(3-chlorophenoxy)-2,3,4,5-tetrahydro-3-benzazepine;
1-(3-chlorophenoxy)-3-methylamino-2,3,4,5-tetrahydro-3-benzazepine;
3-Imidazolethyl-2,3,4,5-tetrahydro-1-(4-(trifluoromethylphenoxy)-3-benzazepine; and
N-[2,3,4,5-Tetrahydro-1-(4-trifluoromethylphenoxy)-3-benzazepin-3-yl]imidazolacetamide.

The following examples are presented in order to illustrate the present invention.

EXAMPLE 1

3-Amino-2,3,4,5-tetrahydro-1-(4-trifluoromethylphenoxy)-3-benzazepine maleate

A solution of sodium nitrite (3 g) in 25 ml water was slowly added to a solution of 2,3,4,5-tetrahydro-1-(4-trifluoromethylphenoxy)-3-benzazepine (free base, 10 g) in 100 ml of 10% aqueous hydrochloric acid. After one hour, the reaction mixture was extracted with dichloromethane. The organic extract was dried (anhydrous magnesium sulfate), filtered and concentrated to a brown oil. This oil was eluted through silica with 30% hexane in dichloromethane via flash column chromotography to yield 9 g of pale yellow oil.

Zinc dust (12 g) was added to a solution of 3-nitroso-2,3,4,5-tetrahydro-1-(4-trifluoromethylphenoxy)-3-benzazepine (9 g) in 150 ml of 2:1 acetic acid/water mixture. After stirring at ambient temperature for three hours, the reaction mixture was filtered, stirred with ice and basified with ammonium hydroxide. The oil which had separated was extracted with dichloromethane. The dried (anhydrous magnesium sulfate) organic extract was filtered and concentrated. The residue was eluted through silica with 3% methanol in dichloromethane via high performance liquid chromatography to yield 6.3 g of white solid, mp 98°–100°. A three gram portion was converted to the maleate salt in 5% methanol/ether to yield 2.7 g of white solid, mp 129°–131°.

Analysis: Calculated for $C_{21}H_{21}F_3N_2O_5$: 57.53% C, 4.83% H, 6.39% N. Found: 57.52% C, 4.87% H, 6.36% N.

EXAMPLE 2

3-Amino-7,8-dimethoxy-1-phenoxy-2,3,4,5-tetrahydro-3-benzazepine maleate

A solution of sodium nitrite (2.1 g) in 10 ml water was slowly added to a solution of 7,8-dimethoxy-1-phenoxy-2,3,4,5-tetrahydro-3-benzazepine (free base, 7 g) in 100 ml of 10% aqueous hydrochloric acid. After one hour, the reaction mixture was extracted with dichloromethane. The organic extract was dried (anhydrous magnesium sulfate), filtered and concentrated to 6 g oil. This oil was eluted through silica with dichloromethane via flash column chromatography to yield 4 g of glassy solid. This was combined with 7.1 g product obtained from two previous batches of nitrosation.

Zinc dust (9 g) was added to a solution of 7,8-dimethoxy-3-nitroso-1-phenoxy-2,3,4,5-tetrahydro-3-benzazepine (10 g) in 150 ml of 2:1 acetic acid/water. After stirring at ambient temperate for three hours, the reaction mixture was filtered, stirred with ice and basified with ammonium hydroxide. The oil which had separated was extracted with dichloromethane. The organic extract was washed with water and saturated sodium chloride solution, and thereafter dried (anhydrous magnesium sulfate), filtered and concentrated to 10 g brown oil. This was eluted through silica with ethyl acetate via high performance liquid chromatography to yield 8.6 g white solid, mp 98°–100°. This solid was again eluted through silica with 5% methanol in dichloromethane via high performance liquid chromatography to yield 6 g white solid, mp 107°–109°. A three gram portion was converted to the maleate salt in 10% methanol/ether to yield 3.3 g white solid, mp 132°–134°.

Analysis: Calculated for $C_{22}H_{26}N_2O_7$: 61.38% C, 6.09% H, 6.51% N. Found: 61.36% C, 5.98% H, 6.47% N.

EXAMPLE 3

3,5-Dichloro-N-(7,8-dimethoxy-1-phenoxy-2,3,4,5-tetrahydro-1H-3-benzazepin-3-yl)benzamide 3,5-Dichlorobenzoyl chloride (1.7 g) was added to a solution of 3-amino-7,8-dimethoxy-1-phenoxy-2,3,4,5-tetrahydro-3-benzazepine (2.1 g) in 100 ml dichloromethane containing sodium bicarbonate (3 g). After one hour, the mixture was filtered and concentrated. The solid residue was eluted through silica with 10% ethyl acetate in dichloromethane to yield 2.4 g of light tan solid, mp 182°–184°. This solid was recrystallized from acetonitrile to yield 2 g of white crystals, mp 184°–185°.

Analysis: Calculated for $C_{25}H_{24}Cl_2N_2O_4$: 61.61% C, 4.96% H, 5.75% N. Found: 61.41% C, 4.84% H, 5.72% N.

EXAMPLE 4

N-[2,3,4,5-Tetrahydro-1-(4-trifluoromethylphenoxy)-3-benzazepin-3-yl]carbamic acid ethyl ester A solution of ethyl chloroformate (3.6 g) in 25 ml dichloromethane was slowly added to a solution of 3-amino-2,3,4,5-tetrahydro-1-(4-trifluoromethylphenoxy)-3-benzazepine (9 g) in 100 ml dichloromethane containing sodium bicarbonate (7 g). After one hour, the reaction mixture was filtered and concentrated to 11 g solid. A 3 g sample was recrystallized from ether to yield 2.2 g white crystals, mp 156°–157°.

Analysis: Calculated for $C_{20}H_{21}F_3N_2O_3$: 60.90% C, 5.37% H, 7.10% N. Found: 61.04% C, 5.46% H, 7.11% N.

EXAMPLE 5

N-Methyl-N-[2,3,4,5-tetrahydro-1-(4-trifluoromethylphenoxy)-3-benzazepin-3-yl]carbamic acid ethyl ester Potassium-t-butoxide (3 g) was added as a powder to an ice-cooled solution of N-[2,3,4,5-tetrahydro-1-(4-trifluoromethylphenoxy)3-benzazepin-3-yl]carbamic acid ethyl ester (8 g) in 100 ml tetrahydrofuran. After thirty minutes, a solution of dimethyl sulfate (3.1 g) in 25 ml tetrahydrofuran was slowly added. After one hour, the reaction mixture was stirred with water and extracted with ethyl acetate. The dried (anhydrous magnesium sulfate) organic layer was filtered and concentrated. The residue was triturated with ether to yield 6 g solid, mp 204°–205°. A 2 gram sample was recrystallized from acetonitrile to yield 1.6 g white crystals, mp 218°–219°.

Analysis: Calculated for $C_{21}H_{23}F_3N_2O_3$: 61.75% C, 5.68% H, 6.86% N. Found: 61.92% C, 5.86% H, 6.88% N.

EXAMPLE 6

N-[2,3,4,5-Tetrahydro-1-(4-trifluoromethylphenoxy)-1H-3-benzazepin-3-yl]trifluoroacetamide Methyl trifluoracetate (4.2 g) was added to a solution of 3-amino-2,3,4,5-tetrahydro-1-(4trifluoromethylphenoxy)-1H-3-benzazepine (8.4 g) in 100 mL anhydrous methanol and triethylamine (3.3 g). The solution was allowed to stand overnight at ambient temperature and thereafter concentrated. The residue was triturated with ether and the resultant product was collected and dried to yield 8.5 g white solid, mp 192°–195°.

Analysis: Calculated for $C_{19}H_{16}F_6N_2O_2$: 54.55% C, 3.86% H, 6.70% N. Found: 54.49% C, 3.94% H, 6.72% N.

EXAMPLE 7

N-Methyl-N-[2,3,4,5-tetrahydro-1-(4-trifluoromethylphenoxy)-1H-3-benzazepin-3-yl] trifluoroacetamide Potassium-t-butoxide (1.4 g) was added as a powder to an ice-cooled solution of N-[2,3,4,5-tetrahydro-1-(4-trifluoromethylphenoxy)-1H-3-benzazepin-3-yl]-trifluoroacet amide (4 g) in 100 mL tetrahydrofuran. After thirty minutes, dimethyl sulfate (1.5 g) was added. After warming to ambient temperature, the reaction mixture was stirred with water and extracted with ethyl acetate.

The dried (anhydrous magnesium sulfate) organic layer was filtered and concentrated to 4.1 g solid, mp 210°-212°. A 2.5 g portion was recrystallized from acetonitrile to yield 1.6 g white crystals, mp 216°-218°.

Analysis Calculated for $C_{20}H_{18}F_6N_2O_2$: 55.55% C, 4.20% H, 6.48% N. Found: 55.62% C, 4.16% H, 6.47% N.

EXAMPLE 8

3-Methylamino-2,3,4,5-tetrahydro-1-(4-trifluoromthylphenoxy)-1H-3-benzazepine maleate Lithium aluminum hydride (1M in tetrahydrofuran, 105 mL) was added slowly to a solution of N-[2,3,4,5-tetrahydro-1-(4-trifluoromethylphenoxy)-1H-3-benzazepin-3-yl] carbamic acid ethyl ester (8 g) in 160 mL tetrahydrofuran. The reaction mixture was stirred twenty hours at 70°-75° and thereafter cooled and quenched by slow addition of a saturated ammonium chloride solution. The mixture was filtered and the organic filtrate was washed successively with water and a saturated sodium chloride soltuion and thereafter dried (anhydrous magnesium sulfate), filtered and concentrated to 7 g oil. This was eluted through silica 50% ethyl acetate in dichloromethane via flash column chromatography to yield 2.6 g pale yellow oil. This was combined with 0.6 g product obtained from a previous reaction and converted to the maleate salt in 5% methanol in ether to yield 1.6 g white crystals, mp 138°-140°.

Analysis: Calculated for $C_{22}H_{23}F_3N_2O_5$: 58.40% C, 5.12% H, 6.19% N. Found: 58.56% C, 4.79% H, 6.15% N.

We claim:

1. A compound of the formula

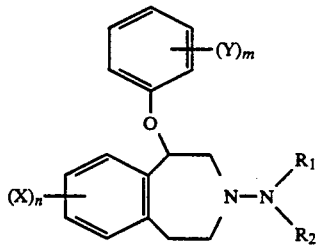

where
n is 1 or 2;
m is 1 or 2;
each X is independently hydrogen or loweralkoxy;
Y is hydrogen, halogen or trifluoromethyl;
R₁ is hydrogen, loweralkyl, arylloweralkyl, heteroarylloweralkyl, pyridinyl, loweralkylcarbonyl, arylloweralkylcarbonyl, heteroarylloweralkylcarbonyl, trifluoromethylcarbonyl or arylcarbonyl; and
R₂ is hydrogen, loweralkyl, loweralkoxycarbonyl, aminoloweralkylcarbonyl, loweralkylaminoloweralklycarbonyl or diloweralkylaminoloweralkylcarbonyl; the term aryl in each occurrence signifying a phenyl group substituted with 0, 1 or 2 substituents each of which being independently loweralkyl, loweralkoxy, halogen or trifluoromethyl, and the term heteroaryl signifying imidazolyl, thienyl, pyridinyl or pyrrolyl;

or a pharmaceutically acceptable acid addition salt thereof.

2. The compound as defined in claim 1, which is 3-amino-2,3,4,5-tetrahydro-1-(4-trifluoromethylphenoxy)-3-benzazepine.

3. The compound as defined in claim 1, which is 3-amino-7,8-dimethoxy-1-phenoxy-2,3,4,5-tetrahydro-3-benzazepine.

4. The compound as defined in claim 1, which is 3,5-dichloro-N-(7,8-dimethoxy-1-phenoxy-2,3,4,5-tetrahydro-1H-3-benzazepin-3-yl)benzamide.

5. The compound as defined in claim 1, which is N-[2,3,4,5-tetrahydro-1-(4-trifluoromethylphenoxy)-3-benzazepin-3-yl]carbamic acid ethyl ester.

6. The compound as defined in claim 1, which is N-methyl-N-[2,3,4,5-tetrahydro-1-(4-trifluoromethylphenoxy)-3-benzazepin-3-yl]-carbamic acid ethyl ester.

7. The compound as defined in claim 1, which is 3-propylamino-2,3,4,5-tetrahydro-1-(4-trifluoromethylphenoxy)-3-benzazepine.

8. The compound as defined in claim 1, which is N-[2,3,4,5-tetrahydro-1-(4-trifluoromethylphenoxy)-3-benzazepin-3-yl]acetamide.

9. The compound as defined in claim 1, which is 3-phenylethylamino-2,3,4,5-tetrahydro-1-(4-trifluoromethylphenoxy)-3-benzazepine.

10. The compound as defined in claim 1, which is 3-amino-7,8-dimethoxy-2,3,4,5-tetrahydro-1-(4-trifluoromethylphenoxy)-3-benzazepine.

11. The compound as defined in claim 1, which is 7,8-dimethoxy-3-methylamino-1-phenoxy-2,3,4,5-tetrahydro-3-benzazepine.

12. The compound as defined in claim 1, which is 3-amino-1-(3-chlorophenoxy)-2,3,4,5-tetrahydro-3-benzazepine.

13. The compound as defined in claim 1, which is 1-(3-chlorophenoxy)-3-methylamino-2,3,4,5-tetrahydro-3-benzazepine.

14. The compound as defined in claim 1, which is 3-Imidazolethyl-2,3,4,5-tetrahydro-1-(4-(trifluoromethylphenoxy)-3-benzazepine.

15. The compound as defined in claim 1, which is N-[2,3,4,5-tetrahydro-1-(4-trifluoromethylphenoxy)-3-benzazepin-3-yl]imidazolacetamide.

16. A pharmaceutical composition which comprises a compound as defined in claim 1 in an amount effective for the treatment of depression and a suitable carrier therefor.

17. A method of treating a patient in need of relief from depression, which comprises administering to such a patient an effective amount of a compound as defined in claim 1.

* * * * *